Figure 1:
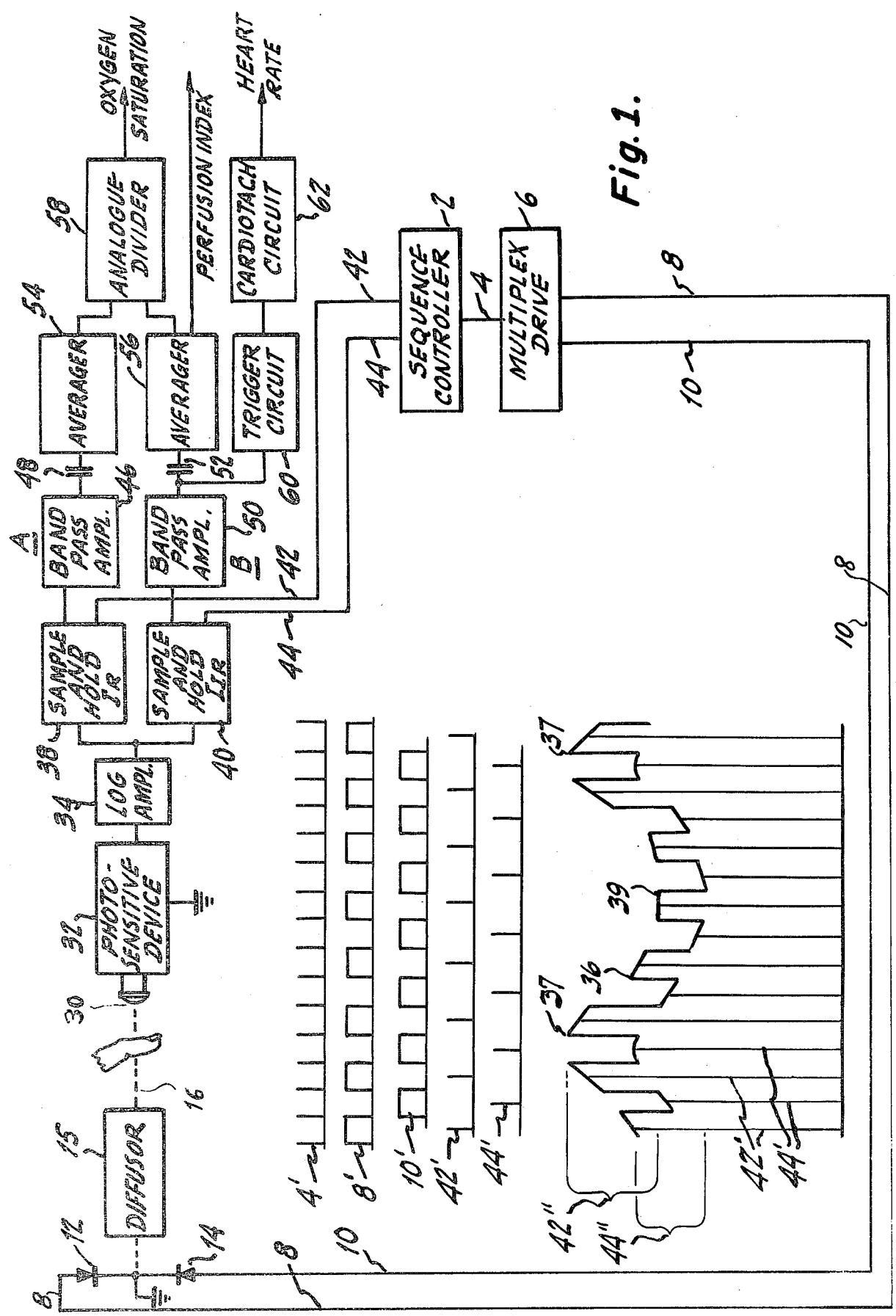

United States Patent [19]

Nielsen

[11] 4,167,331

[45] Sep. 11, 1979

[54] MULTI-WAVELENGTH INCREMENTAL ABSORBENCE OXIMETER

[75] Inventor: Larry L. Nielsen, Burlington, Mass.

[73] Assignee: Hewlett-Packard Company, Palo Alto, Calif.

[21] Appl. No.: 752,494

[22] Filed: Dec. 20, 1976

[51] Int. Cl.$^2$ ............................................. G01N 33/16
[52] U.S. Cl. ..................................... 356/39; 128/633; 356/40; 356/41
[58] Field of Search ............................ 356/39, 40, 41; 128/2 L

[56] References Cited

U.S. PATENT DOCUMENTS

| | | | |
|---|---|---|---|
| 3,638,640 | 2/1972 | Shaw | 356/41 |
| 3,647,299 | 3/1972 | Lavallee | 356/41 |
| 3,704,706 | 12/1972 | Herczfeld et al. | 356/41 |
| 3,804,535 | 4/1974 | Rodriguez | 356/41 |
| 3,998,550 | 12/1976 | Konishi et al. | 356/41 |

*Primary Examiner*—Vincent P. McGraw
*Attorney, Agent, or Firm*—Donald N. Timbie

[57] ABSTRACT

Light of two different wavelengths is passed through or reflected from a member of the body so as to be modulated by the pulsatile blood flow therein. The amplitudes of the alternating current components of the logarithms of the respective light modulations are compared by taking their molecular extinction coefficients into account so as to yield the degree of oxygen saturation. By adding a third wavelength of light, the percentage of other absorbers in the blood stream such as a dye or carboxyhemoglobin can be measured. Fixed absorbers reduce the amount of light that passes through or is reflected from the body member by a constant amount and so have no effect on the amplitudes of the alternating current components that are used in making the measurements.

7 Claims, 4 Drawing Figures

MULTI-WAVELENGTH INCREMENTAL ABSORBENCE OXIMETER

BACKGROUND OF THE INVENTION

The degree of oxygen saturation of arterial blood is often a vital index of the condition of a patient. Whereas apparatus is available for making accurate measurements on a sample of blood in a cuvette, it is not always possible or desirable to withdraw blood from a patient, and it is obviously impracticable to do so when continuous monitoring is required. Therefore, much effort has been expended in devising an instrument for making the measurement by non-invasive means.

One approach has been to substitute a portion of the body such as a lobe of the ear for the cuvette and measure the difference in light absorption between oxyhemoglobin $HbO_2$ and deoxyhemoglobin Hb. Unfortunately, however, complications are introduced by the presence of a large number of light absorbers other than $HbO_2$ and Hb, including, for example, skin and hair.

The following considerations are fundamental to the problem. As blood is pulsed through the lungs by heart action a certain percentage of the deoxyhemoglobin, Hb, picks up oxygen so as to become oxyhemoglobin, $HbO_2$. By medical definition the oxygen saturation $SO_2 = HbO_2/(Hb + HbO_2)$. It is this fraction which is to be determined. From the lungs the blood passes through the arterial system until it reaches the capillaries at which point a portion of the $HbO_2$ gives up its oxygen to support the life process in adjacent cells. At the same time the blood absorbs waste matter from the cells and is made to flow steadily back to the heart by the vascular system.

Increasing the blood flow or perfusion in the ear increases the amount of blood and therefore the amount of $HbO_2$ reaching the capillaries to such degree that the oxygen thus supplied can far exceed the amount of oxygen consumed by the cells, thereby making the oxygen content of the venous blood nearly equal to the oxygen content of the arterial blood. Inasmuch as the light must obviously pass through both arterial as well as venous blood, the measurement of the relative amounts of Hb and $HbO_2$ yields an oxygen saturation measurement of $SO_2$ that approaches the value for arterial blood alone. Unfortunately, the condition of some patients, for example a patient in shock, is often such as to prevent the attainment of sufficient perfusion to yield highly accurate results.

Wood, as described in his U.S. Pat. No. 2,706,927, suggested a way of computing the oxygen saturation from measurements of light absorption at two wavelengths taken under two conditions, (1) a "bloodless" condition in which as much blood as possible is squeezed from the earlobe and (2) a condition of normal blood flow. It was hoped that the "bloodless" measurement would be affected only by the absorbers other than blood and that the normal blood flow measurement would be affected by both the other absorbers and the blood so that a comparison of the readings would indicate the absorption by the blood alone. Unfortunately, the accuracy of the measurements is seriously impaired, not only by the fact that squeezing does not eliminate all the blood but also because it changes the optical coupling between the ear and the optical apparatus. Furthermore, because of wide variations between patients in the effect of absorbers, such as the pigment of the skin and its thickness, a separate calibration must be made for each patient and for each measurement.

Many of these problems have been overcome by apparatus suggested by Shaw in his U.S. Pat. No. 3,638,640 in which light absorption measurements are taken at a number of wavelengths of light. However, in this as well as in all other prior art apparatus, good results have depended on increasing the perfusion in the member of the body being measured so that the blood therein is as close to arterial blood as possible. Whereas perfusion can be increased by artificial methods to the point where accurate results are obtained, there are many situations when the patient's condition makes such methods undesirable or even impossible.

BRIEF DESCRIPTION OF AN EMBODIMENT OF THIS INVENTION

If Hb and $HbO_2$ are the only light absorbers of significance in the arterial blood stream, the degree of oxygen saturation can be accurately determined, in accordance with this invention, in the following general way. Light of one wavelength and light of another wavelength are sequentially directed to a given area on a finger, a lobe of the ear, or other body member. Photosensitive means are positioned so as to produce a first electrical signal that is proportional to light of the one wavelength after a portion of it has been absorbed by the body member and a second electrical signal after a portion of light of the other wavelength has been absorbed by the body member. When the heart forces more blood into the arterial system, there is more volume of blood in the body member so that light of both wavelengths is attenuated more than when the heart is at rest. Thus, both first and second electrical signals have maximum and minimum peaks occurring during a heart cycle. It is important to note that the difference between the peaks is due entirely to the pulsatile arterial blood flow and that it is completely unaffected by light absorbers that attenuate the light by constant amounts throughout the heart cycle.

For reasons that will be explained at a later point, the light absorbed by any absorber is directly proportional to the log of the light after it has been attenuated by the absorber. Means are provided for deriving a first output signal that varies as the peak to peak amplitude of the log of said first electrical signal, and means are also provided for deriving a second output signal that varies as the peak to peak amplitude of the log of said second electrical signal. Each ratio of the first and second output signals corresponds to a different percent of the oxygen saturation $SO_2$. Therefore, the percent of $SO_2$ can be determined from a graph or it can be automatically derived from a read only memory that is programmed with the percent $SO_2$ that corresponds to each ratio. Of course this requires that the ratio be digitized. It is also possible to use a microprocessor to make the calculation.

In some cases it may be desired to also determine the percent saturation of another light absorbing blood component such as carboxyhemoglobin, HbC. To do this three wavelengths of light are separately and sequentially directed to the member of the body selected. The photosensitive device and the logging means are the same as before but the voltage at their output is now sequentially applied to three channels in synchronism and phase with the sequential operation of the lights. Each channel is the same as before, but because there are three of them the percentage saturations of oxygen and the other components cannot be determined by a simple ratio. However, as will be explained, the pulsatile output signal of each channel is equal to the sum of the absorptions of the three absorbers of interest for the particular wavelength of light in that channel. This yields three simultaneous equations that can be solved. It is most convenient to apply the signals to an A.D. converter and then to a microprocessor. The percentage saturation of any number of pulsatile absorbers can be determined in this way simply by using the same number of different wavelengths of light and the same number of channels. As will be shown, apparatus constructed in accordance with this invention can readily yield other valuable information such as cardiac output, perfusion index and heart rate.

THE DRAWINGS

Figure 2:
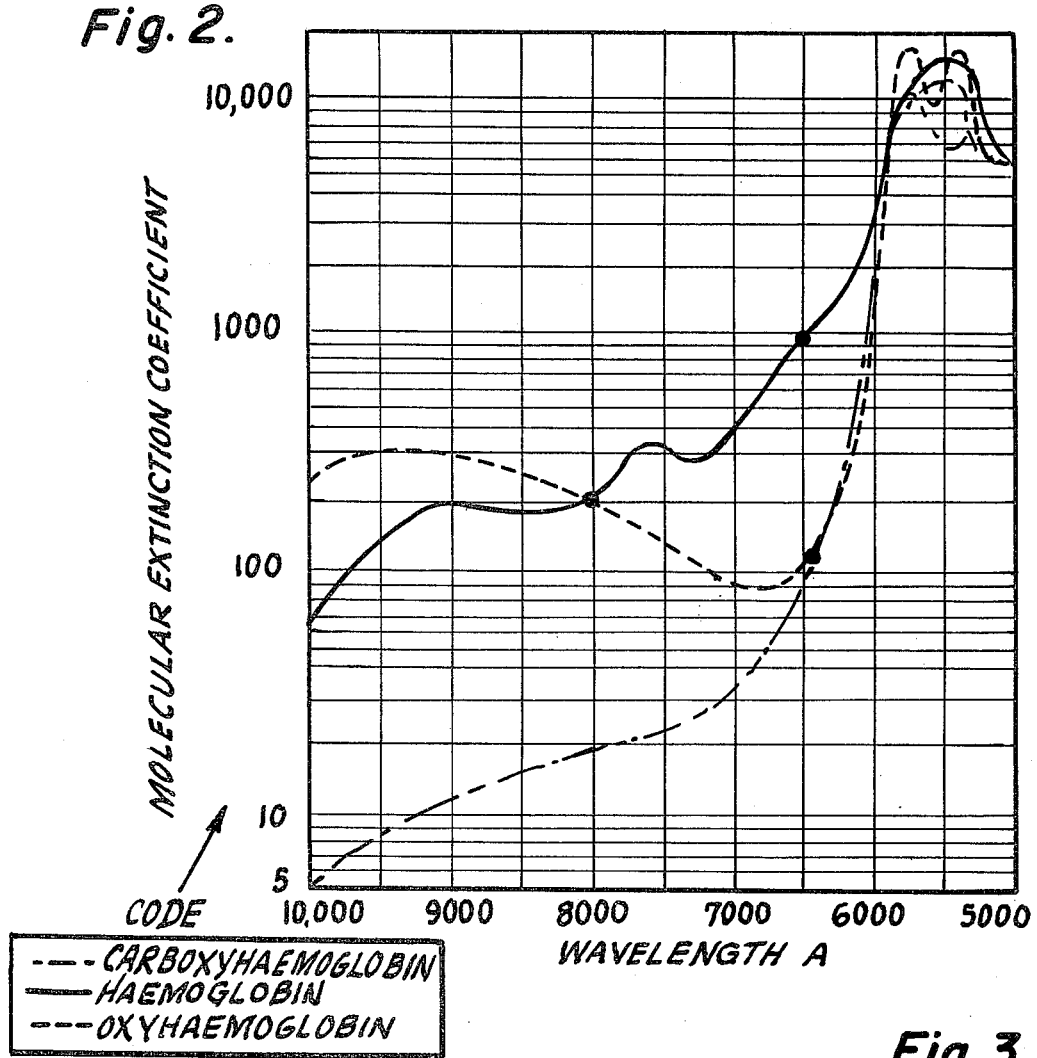
Figure 3:
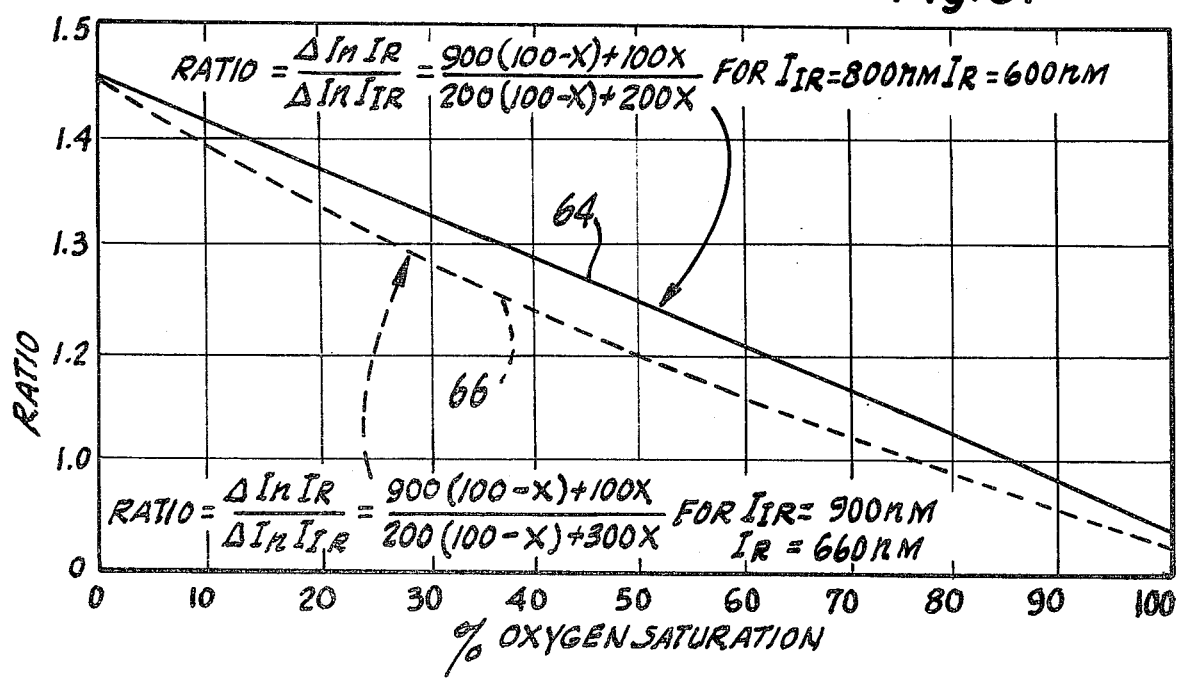
Figure 4:
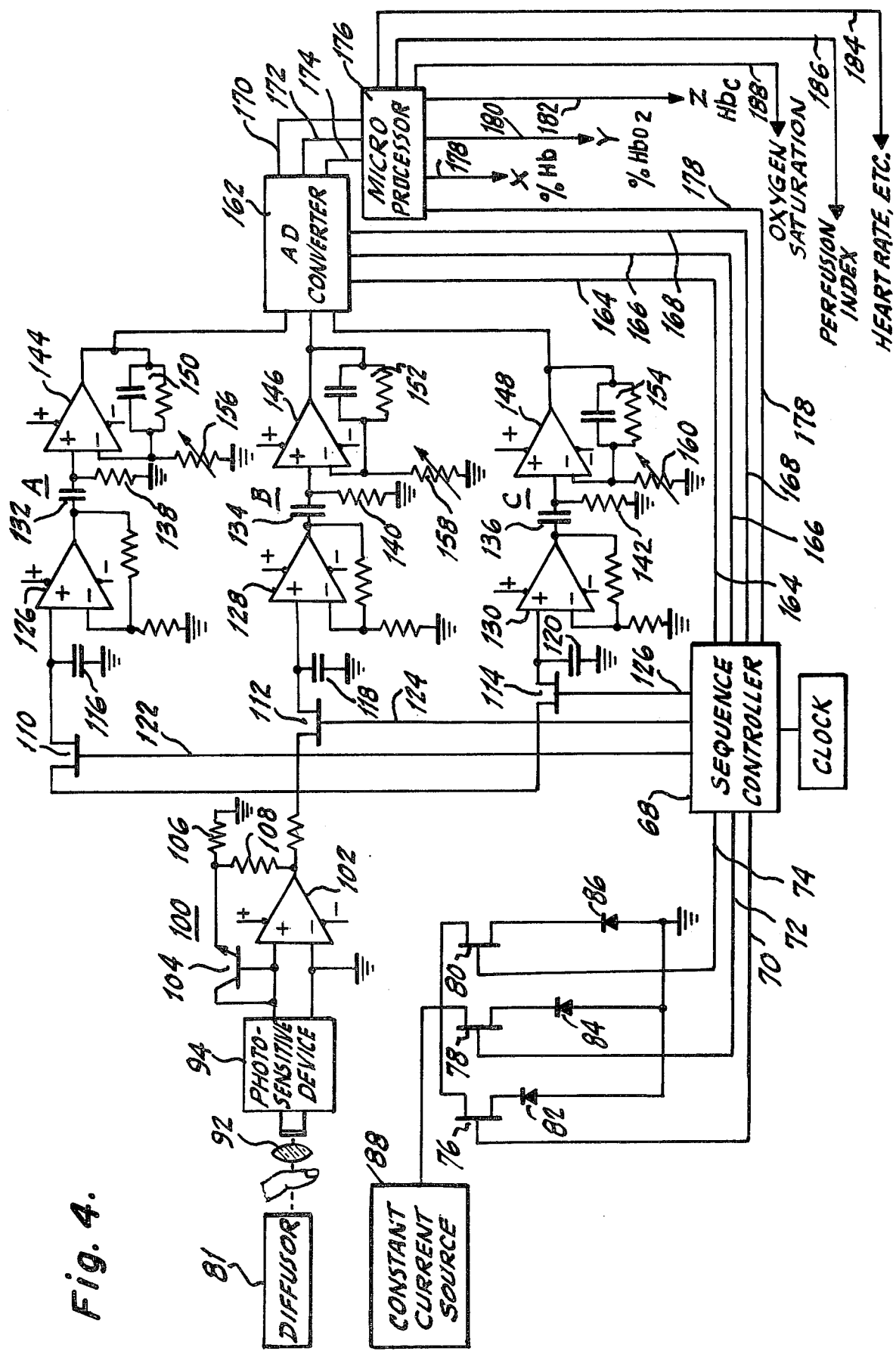

FIG. 1 is a diagram of an oximeter utilizing light of two wavelengths,

FIG. 2 includes graphs showing the way the molecular extinction coefficient varies with the wavelength of light of Hb, $HbO_2$, and HbC, FIG. 3 includes graphs showing the relationship between the ratio of the pulsatile signals provided by the two channels of the oximeter of FIG. 1 vs. the percentage oxygen saturation for combinations of the two, and FIG. 4 is a diagram of an oximeter utilizing light of three wavelengths in order to detect the percentage of a third light absorber in the arterial blood.

DESCRIPTION OF AN EMBODIMENT OF THE INVENTION

In the apparatus illustrated in FIG. 1, the timing of all circuit functions is determined by a sequence controller 2. At an output 4, it provides a series of equally spaced pulses 4' at a pulse repetition frequence f. In response to these pulses a multiplex drive 6 provides pulses 8' on an output lead 8 and pulses 10' on an output lead 10. The positive pulses 8' and 10' have a frequency of f/2, a duration equal to the time between successive pulses 4' and are interleaved. Light emitting diode 12 that emits light of a wavelength $\lambda_1$ and light emitting diode 14 that emits light of a wavelength $\lambda_2$ are connected between the leads 8 and 10 in such polarity that the diode 12 is turned on during the pulses 8' and the diode 14 is turned on during the interleaved pulses 10'. Although the pulses 8' and 10' are shown as having the same amplitude, the amplitudes may be different if this is required to cause the intensity of the light emitted by each diode to be as desired.

One embodiment is an array of suitably placed light emitting diodes. This array may be comprised of discrete light emitting diodes or diode chips mounted within a common package. In either case, light from the diodes 12 and 14 is passed through an optical diffuser 15. If desired, light pipes could be used to conduct light from each light emitting source to the input of the diffuser 15. Light from either diode appears at the output surface of the diffuser 15 so that it will pass into the same area of the body member with which the output of the diffuser is in contact.

It is intended that a member of the body such as a finger, as shown, or the lobe of an ear, be inserted in the path 16 between the diffusor 15 and a collection lens 30 of a photosensitive device 32 which would normally be in optical contact with the finger or other body member.

The current, i, generated by the photosensitive device 32 is applied to the input of an amplifier 34 that produces voltage at its output that is a logarithmic function of the current, i, and is represented by the wave 36. Because the body member absorbs less of the light of wavelength $\lambda_1$ than of light of wavelength $\lambda_2$, the wave 36 has a greater amplitude during the pulses 8' than during the pulses 10'. The large peaks, 37, of the wave 36 occur when the blood pressure is at the low point of its cycle because less blood is in the path 16 to absorb the light. Conversely, the trough 39 of the wave 36 occurs at the high pressure point in the heartbeat cycle when more blood is in the path 16 to absorb the light. The time between the peaks 37 is therefore related to the heart rate and is approximately one second. The frequency of the pulses 4 is relatively much higher than illustrated.

In the interest of simplicity the wave 36 is drawn as though there were no delay in the optical apparatus just described, but in practice, time must be allowed for settling. For this reason the pulses 42' provided by the sequence controller 2 on a lead 42 for the purpose of causing the sample and hold circuit 38 to sample the voltage wave 36 are timed to occur halfway through the pulses 8'. Similarly, the pulses 44' provided by the sequence controller 2 on a lead 44 for the purpose of causing the sample and hold circuit 40 to sample the voltage wave 36 are timed to occur halfway through the pulses 10'. Each sample and hold circuit produces an output voltage that is the same value as the value of one sample until the next sample is taken. The output voltage of the sample and hold circuit 38 therefore, very closely corresponds to a wave drawn through the peaks of the samples 42', and the output voltage of the sample and hold circuit 40 very closely corresponds to a wave drawn through the peaks of the samples 44'. The peak to peak amplitude of these waves, as indicated by the brackets 42" and 44", is proportional to the amount of pulsatile blood. The ratio of these amplitudes yields information as to the degree of oxygen saturation.

It is an important part of this invention to provide means for passing the A.C. components and blocking the D.C. components of the outputs of the sample and hold circuits. For this purpose a bandpass amplifier 46 and a capacitor 48 are coupled to the output of the sample and hold circuit 38 and a bandpass amplifier 50 and a capacitor 52 are coupled to the output of the sample and hold circuit 40. The axis of these A.C. waves may be at different D.C. levels depending on the effect of constant absorbers such as hair, the venous blood flow and the pigmentation and thickness of the skin through which the lights pass, but this has no effect on the A.C. voltage waves at the output sides of the capacitors 48 and 52. The only absorbers that have any effect are those contained in the arterial blood flow, and they are the only ones of interest.

Any suitable means 54 and 56 can be respectively coupled to the capacitors 48 and 52 for the purpose of deriving an output signal, usually a voltage, that varies as the average value of the A.C. waves above their lowest values. One could also use a clamp circuit and an integrator, a peak to peak detector, or even a full wave rectifier. As will be explained, it is the ratio of these average values that yields the information as to the desired degree of oxygen saturation $SO_2$. The ratio can be determined by simple division or by an analogue divider 58, and the degree of oxygen saturation can be determined from a graph of the ratio vs. $SO_2$, or, if the ratio is digitized, it can be applied to a preprogrammed read only memory or R.O.M. so as to yield the value of SO₂ directly.

Other useful information can be derived by the apparatus just described, e.g., the degree of perfusion can be attained directly from the output of either averaging means 54 or 56 because the average values of either A.C. wave are directly proportional to the arterial blood flow. In fact, if only one of the channels A or B is used, the apparatus is the same as the perfusion apparatus described in the U.S. Patent application Ser. No. 696,973, now Patent No. 4,109,643, entitled "Perfusion, Meter" filed on June 17, 1976 in the name of Edwin B. Merrick. It is also possible to determine the heartbeat rate by applying the A.C. output of either of the bandpass amplifiers 46 or 50 to a trigger circuit 60 and coupling its output to a cardiotachometer circuit 62.

Theory of Operation

In accordance with the Lambert-Beers Law, the ratio of light I of a single wavelength that is transmitted by an optically absorbing material or tissue to the incident light $I_o$ of the same wavelength is given by the expression $$I/I_o = e^{-Ecd} = e^{-A} \qquad (1)$$

wherein c is the concentration of the absorber, d its thickness and E the molecular extinction coefficient of the absorber for the particular wavelength of light employed. It is convenient to refer to the product Ecd as the absorption A.

By taking the log of both sides of (1) we obtain an expression for the absorption A $$-\ln I/I_o = Ecd = A. \qquad (2)$$

Now, if the light is incident on a mixture of substances, each having its own concentration and thickness, the total absorption is equal to the sum of the absorptions of each substance. Thus, if CHb and CHbO₂ are the respective concentrations of the deoxyhemoglobin and the oxyhemoglobin in the blood, Cn is the concentration of any fixed absorber such as skin or hair, if dHb, dHbO₂ and dN are the corresponding thicknesses of each; and if EHb, EHbO₂ and EN are the corresponding molecular extinction coefficients, we can say for any particular wavelength of light that $$-\ln I/I_o = EHb\ CHb\ dHb + EHbO_2\ CHbO_2\ dHbO_2 + EN\ Cn\ dN = A. \qquad (3)$$

If blood is pulsing through the portion of a body member in the path 16 of FIG. 1, the absorption due to the components of the blood will be changing with time while in the absence of movement of the position of the body member in the path 16 with respect to the optical system, the absorption of all other components such as skin, hair, etc. remains constant and does not change with time. Thus, by taking the derivative of (3) with respect to time we obtain $$-d/dt \ln I/I_o = d/dt\ EHb\ CHb\ dHb + d/dt\ EHbO_2\ CHbO_2\ DHbO_2 + d/dt\ EN\ CN\ dN = d/dt\ A, \qquad (4)$$

but the last term is zero because it is the derivative of a constant.
Furthermore $$-d/dt \ln I/I_o = -d/dt \ln I - d/dt \ln I_o \qquad (5)$$

and if $I_o$ is maintained constant, its derivative is also zero, so that $$-d/dt \ln I = d/dt\ EHb\ CHb\ dHb + d/dt\ EHbO_2\ CHbO_2\ dHbO_2 = d/dt\ A. \qquad (6)$$

Equation (6) shows that, in the absence of field motion, the changes in the logarithm of the transmitted light I are directly proportional to the changes in the combined absorptions of the deoxyhemoglobin and the oxyhemoglobin, or in other words, to the change in absorption of the pulsatile or arterial blood. Thus, with a single wavelength of light we can obtain an indication of the relative volume or perfusion of the blood.

Now let us assume that the photosensitive device 32 is a diode wherein the current i generated therein by the transmitted light I can be expressed for the selected wavelength of light as $$i = kI \qquad (7)$$

where k is a constant related to the particular diode used and the wavelength of light involved. When the current is passed through the logging amplifier 34, we obtain an output voltage v that may be expressed as $$v = a \ln i = a \ln kI = a \ln k + a \ln I, \qquad (8)$$

where a is a constant relating the output voltage to the input current of the amplifier 34. Now if we look at only the A.C. component of this voltage as previously discussed in connection with the bandpass amplifier 46 and the capacitor 48, we have $$\Delta v = a\Delta \ln i = a\Delta \ln k + a\Delta \ln I \qquad (9)$$

and inasmuch as the change in the natural log of a constant k is zero we can say that the A.C. component, $\Delta v_1$ at the output of the log amplifier 34 is $$\Delta v_1 = a\Delta \ln i = a\Delta \ln I = a\Delta A = a\Delta\ EHb\ CHb\ dHb + a\Delta\ EHbO_2\ CHbO_2\ dHbO_2. \qquad (10)$$

There are two important properties to note about this time-varying log function; first, all fixed absorbers (skin, pigmentation, cartilage, bone, hair, venous blood, etc.) have no influence on the final voltage; second, all system gain factors drop out of the final equation if they can be considered to multiply $I_o$ and are non-time varying.

Separation of Hb and HbO₂

In order to determine the oxygen saturation, SO₂, we need to separate the absorption of Hb from that of HbO₂. If we use two wavelengths of light, e.g., red, $I_R$ at 660 nM and infrared $I_{IR}$ at 800 nM, for example, then the ratio of the amplitude of the A.C. voltage, v, at the output of channel A of FIG. 1 to the amplitude of the A.C. voltage at the output of channel B may be expressed as the ratio of equations (10) for each wavelength, or $$\frac{a\Delta \ln I_R}{a\Delta \ln I_{IR}} = \frac{a\Delta E_{RHb} C_{Hb} d_{Hb} + a\Delta E_{RHbO_2} C_{HbO_2} d_{HbO_2}}{a\Delta E_{IRHb} C_{Hb} d_{Hb} + a\Delta E_{IRHbO_2} C_{HbO_2} d_{HbO_2}} \qquad (11)$$

The concentration-distance product $C_b d_b$ for the pulsatile blood as a whole is equal to the sum of each of the absorption components. Thus, if the only components are assumed to be $H_b$ and $HbO_2$, their percentages can be expressed as $(100-x)$ and x. Thus:

$$C_b d_b = (C_{Hb} d_{Hb} + C_{HbO_2} d_{HbO_2}) = (100-x)C_b d_b + x C_b d_b \qquad (12)$$

By using the above and observing that the a and $C_b d_b$ cancel, equation (11) becomes:

$$\frac{\Delta \ln I_R}{\Delta \ln I_{IR}} = \frac{\Delta E_{RHb}(100-x) + \Delta E_{RHbO_2} x}{\Delta E_{IRHb}(100-x) + \Delta E_{IRHbO_2} x} \qquad (13)$$

Reference to FIG. 2 shows the molecular extinction coefficient for the chosen wavelength of IR=800 nM to be 200 for both Hb and $HbO_2$ but at the chosen wavelength of R=660 nM, $E_{RHb}=900$ and $E_{RHbO_2}=100$. Substituting these values in (13) yields $$\frac{\Delta \ln I_R}{\Delta \ln I_{IR}} = \frac{900(100-x) + 100x}{200(100-x) + 200x} \qquad (14)$$

This is the equation of a straight line that is represented by the line 64 in the graph of FIG. 3. One end point of the line 64 is established by making the concentration $C_{HbO_2}$=to zero, i.e., let x=0. When this is done (14) becomes $$\frac{\Delta \ln I_R}{\Delta \ln I_{IR}} = \frac{900(100-0) + 0}{200(100-0) + 0} = \frac{900}{200} = 4.5 \qquad (15)$$

Then in order to establish the other end point let x=100 and $$\frac{\Delta \ln I_R}{\Delta \ln I_{IR}} = \frac{900(100-100) + 100 \cdot 100}{200(100-100) + 200 \cdot 100} = \frac{1}{2} \qquad (16)$$

Thus the change in voltage $V_R$ in channel A of FIG. 1 divided by the change in voltage $V_{IR}$ in channel B of FIG. 1 yields a ratio shown on the ordinate of the graph of FIG. 3, and the corresponding degree of oxygen saturation $SO_2$ is at the abcissa.

Use of 900 nM for IR

There is no known commercially available light emitting diode for producing an IR of precisely 800 nM where the molecular extinction coefficients are conveniently the same for both Hb and $HbO_2$. Whereas light of this wavelength could be produced by use of an incandescent light source and filter at 800 nM, or by other means known to those skilled in the art, it is simpler and far less expensive to use a commercially available source of light having a wavelength of 900 nM. At this wavelength the molecular extinction coefficient obtained from the graph for Hb in FIG. 2 is 200 and the coefficient for $HbO_2$ is 300. Substituting these values in (13) yields $$\frac{\Delta \ln I_R}{\Delta \ln I_{IR}} = \frac{900(100-x) + 100x}{200(100-x) + 300x} \qquad (17)$$

Substitution of various values of x produces the dotted line 66 of FIG. 3. Although this line is non-linear it is perfectly usable and has the same properties as mentioned above.

Three Wavelength Oximeter

In describing two wavelength oximeter of FIG. 1, it was assumed that the principle absorbers in the arterial blood flow were Hb and $HbO_2$, but it is sometimes of importance to know the percentage of a third absorber such as carboxyhemoglobin, HbC, in which case three wavelengths of light and three channels are used.

In FIG. 4, a sequence controller 68 provides pulses in sequence via the leads 70, 72 and 74 to the gate electrodes of three FETs 76, 78 and 80 that have their source and drain electrodes respectively connected in series with light emitting diodes 82, 84 and 86 between ground and a source 88 of constant current so that the diodes respectively emit light of three different wavelengths in sequence. These wavelengths may be 660 nM, 800 nM and 900 nM. Any suitable means such as a diffuser 89 can be provided for directing light from each diode along a common path 90 to a collection lens 92 for a photosensitive device 94.

The output current i generated by the photosensitive device 94 sequentially corresponds in amplitude to the intensity of light that passes through the body member from the diodes 82, 84 and 86. This current is applied to means such as a logging amplifier 100 for producing an output voltage that is a logarithmic function of the current. In particular, the grounded side of the output of the photosensitive device is connected to the inverting input of an operational amplifier 102 and the output current i is applied to the non-inverting input. The base and collector electrodes of an NPN transistor 104 are connected together and to the non-inverting input of the amplifier, and the emitter of the transistor 104 is connected via a resistor 106 to ground and by a resistor 108 to the output of the operational amplifier 100. A diode could be substituted for the transistor 104, but the connection of the transistor in the manner described greatly increases the accuracy of operation.

The output voltage of the logging amplifier 100 is applied to the source electrodes of FETs 110, 112 and 114, that have their drain electrodes respectively connected to capacitors 116, 118 and 120 so as to form sample and hold circuits for the three channels A, B and C. The sequence controller 68 provides short keying pulses via leads 122, 124 and 126 to the gate electrodes of the FETs 110, 112 and 114 that respectively occur near the middle of the pulses of light emitted by the diodes 82, 84 and 86. The timing of the keying pulses in this manner allows for the inherent delay in the optical system and permits the output voltage of the logging amplifier 100 to reach its maximum value in response to each pulse of light before a sample is taken. When the FETs 110, 112, and 114 are placed in a conducting condition by a keying pulse, the capacitors 116, 118 and 120 are respectively charged or discharged to the value of the output voltage of the logging amplifier 100 that exists at that moment. After the short keying pulse terminates, a capacitor retains its charge until the next keying pulse is applied to the FET.

During the time between keying pulses the voltage across the capacitors 116, 118 and 120 is applied to the non-inverting inputs of operational amplifiers 126, 128 and 130. The outputs of each amplifier is connected to ground via series gain control resistors having their junction connected to the respective inverting inputs of the amplifier. A.C. components of the output voltages of the amplifiers 126, 128 and 130 are respectively coupled via capacitors 132, 134 and 136 to the ungrounded ends of resistors 138, 140 and 142. The ungrounded ends of these resistors are respectively connected to the non-inverting inputs of operational amplifiers 144, 146 and 148. The outputs of the operational amplifiers 144, 146 and 148 are respectively connected to ground via the parallel combinations 150, 152 and 154 of a capacitor and resistor connected in series with variable resistors 156, 158 and 160. With these connections the operational amplifier 144, 146 and 148 function as bandpass amplifiers with sufficient bandwidth to pass the frequency of the keying pulses applied to the FETs and enough sidebands to define the pulses of arterial blood such as are represented by the curve 36 of FIG. 1.

The outputs of the amplifiers 144, 146 and 148 are applied to an A to D converter 162 which is controlled by timing pulses from the sequence controller 68 on leads 164, 166 and 168 in such manner that the digitalized outputs of the amplifiers 144, 146 and 148 appear on the leads 170, 172 and 174 respectively. These leads are connected to a microprocessor 176 which is timed by pulses supplied to it by the sequence controller 68 on a lead 178 so as to make calculations to be described after each sequence of keying pulses have been applied to the gate electrodes of the FETs 110, 112 and 114. Continuous readings of the percent Hb, percent HbO₂ and percent HbC appear at the output leads 178, 180 and 182 of the microprocessor 176, and readings of the heart rate and perfusion index and oxygen saturation (SO₂) appear on output leads 184, 186 and 188 respectively. Additionally, cardiac output could be calculated using a standard dye-dilution procedure.

Operation of FIG. 4

In this explanation the wavelengths of the light emitted by the light emitting diodes 82, 84 and 86 are assumed to be as follows:

$$\lambda_{82} = 660 \text{ nM}$$

$$\lambda_{84} = 800 \text{ nM}$$

$$\lambda_{86} = 900 \text{ nM}$$

In discussing the operation of FIG. 1, it was shown that changes in the log of the light I passing through the body member equals the sum of the changes in absorption by the various absorbers. Therefore, when considering three absorbers Hb, HbO₂ and the carboxyhemoglobin HbC it can be said $$\Delta \ln I_{82} = \Delta E_{Hb}(\lambda_{82}) C_{Hb} d_{Hb} + \Delta E_{HbO_2}(\lambda_{82}) C_{HbO_2} d_{HbO_2} + \Delta E_{HbC}(\lambda_{82}) C_{HbC} d_{HbC}. \quad (18)$$

$$\Delta \ln I_{84} = \Delta E_{Hb}(\lambda_{84}) C_{Hb} d_{Hb} + \Delta E_{HbO_2}(\lambda_{84}) C_{HbO_2} d_{HbO_2} + \Delta E_{HbC}(\lambda_{84}) C_{HbC} d_{HbC}. \quad (19)$$

$$\Delta \ln I_{86} = \Delta E_{Hb}(\lambda_{86}) C_{Hb} d_{Hb} + \Delta E_{HbO_2}(\lambda_{86}) C_{HbO_2} + \Delta E_{HbC}(\lambda_{86}) C_{HbC} d_{HbC}. \quad (20)$$

The concentration-distance product $C_b d_b$ for the pulsatile blood as a whole is equal to the sum of the concentration-distance products for each of the components. Thus, if the only components are assumed to be Hb, HbO₂ and HbC and if their percentages of the whole are respectively X, Y and Z, the equations (18), (19) and (20) can be respectively written as follows:

$$\Delta \ln I_{82} = \Delta E_{Hb}(\lambda_{82}) X C_b d_b + \Delta E_{HbO_2}(\lambda_{82}) Y C_b d_b + \Delta E_{HbC}(\lambda_{82}) Z C_b d_b. \quad (21)$$

$$\Delta \ln I_{84} = \Delta E_{Hb}(\lambda_{84}) X C_b d_b + \Delta E_{HbO_2}(\lambda_{84}) Y C_b d_b + \Delta E_{HbC}(\lambda_{84}) Z C_{hdb}. \quad (22)$$

$$\Delta \ln I_{86} = \Delta E_{Hb}(\lambda_{86}) X C_b d_b + \Delta E_{HbO_2}(\lambda_{86}) Y C_b d_b + \Delta E_{HbC}(\lambda_{86}) Z C_{bde}. \quad (23)$$

Substitution of the extinction coefficients of Hb, HbO₂ and HbC for the different wavelengths of light, as shown in the graphs of FIG. 2, factoring out $C_b d_b$ in the equations (21), (22) and (23) and remembering that in the discussion of the operation of FIG. 1, it was shown that the change in voltage, $\Delta v$, at the output of a channel, like channels A, B or C in FIG. 4, was equal to $\Delta \ln I$, it can be said for similar reasons that the change in voltage $\Delta v_{82}$ at the output of channel A of FIG. 4 is equal to $\Delta \ln I_{82}$; the output of channel B, $\Delta v_{84} = \Delta \ln I_{84}$, and the output of channel C, $\Delta v_{86} = \Delta \ln I_{86}$ so as to yield $$\Delta \ln I_{82} = \Delta(900X + 100Y + 80Z) C_b d_b = \Delta v_{82} \quad (24)$$

$$\Delta \ln I_{84} = \Delta(200X + 200Y + 17Z) C_b d_b = \Delta v_{84} \quad (25)$$

$$\Delta \ln I_{86} = \Delta(200X + 300Y + 10Z) C_b d_b = \Delta v_{86} \quad (26)$$

These simultaneous equations (24), (25) and (26) can be solved by use of determinants as indicated by the equations (27), (28) and (29) below and, as would be apparent to one skilled in the art, they can be evaluated by a microprocessor 176.

$$100X = \%Hb = \frac{|DX|}{|D|} = \frac{\begin{vmatrix} 82 & 100 & 80 \\ 84 & 200 & 17 \\ 86 & 300 & 10 \end{vmatrix}}{|D|C_b d_b} \Delta C_b d_b \quad (27)$$

$$100Y = \%HbO_2 = \frac{|DZ|}{|D|} = \frac{\begin{vmatrix} 900 & 82 & 80 \\ 200 & 84 & 17 \\ 200 & 86 & 10 \end{vmatrix}}{|D|C_b d_b} \Delta C_b d_b \quad (28)$$

$$100Z = \%HbC = \frac{|DZ|}{|D|} = \frac{\begin{vmatrix} 900 & 100 & 82 \\ 200 & 200 & 84 \\ 200 & 300 & 88 \end{vmatrix}}{|D|C_b d_b} \Delta C_b d_b \quad (29)$$

Effect of HbC on Two Wavelength Oximeter

As long as the only pulsatile light absorbers in the blood are Hb and HbO₂, the two wavelength oximeter of FIG. 1 yields accurate results, but even when a third absorber such as HbCO is present in reasonable quantities, this accuracy is still very good. Assume, for example, that the two wavelengths of the light are used are 660 nM and 900 nM and that the percentages of Hb, HbO₂ and HbC are 44, 44 and 12 respectively. Since by definition SO₂=HbO₂/(Hb+HbO₂), SO₂ is 50%. In order to yield this result the ratio of the output voltages of the two channels would have to be exactly 2, as seen from the graph 66 of FIG. 3. This is what the ratio of the equations (24) and (26) would yield if the Z terms were ignored, but since HbCO is present, the consequent inclusion of the Z terms yields a ratio of 2.03. The coordinate value of SO₂ for this ratio from the curve 66 for the two wavelength oximeter is 51%, an error of only 1% of maximum reading.

In the discussion of FIG. 1 the photosensitive device was assumed to have a linear relationship between the light I falling on it and the current, i, which it generated. However, devices having non-linear relationships can be used. For example, let the device have a resistance that is affected by the light in the following way.

$$R = AI^k \quad (30)$$

where R = the photoconductive resistance, I, the illumination and A and k are constants depending on the material. A constant voltage E is applied across the device so that the current i it produces is $$i = (E/R) = (E/AI^k) \quad (31)$$

When the current, i, passes through a logging amplifier, it produces an output voltage, v, that is proportional to the ln i, which is $$v = \ln i = \ln E - \ln A - K \ln I \quad (32)$$

Both FIG. 1 and FIG. 4 include means for deriving a voltage v at the outputs of the channels that is proportional to the pulsatile change in the log of the current i with time so that $$\frac{dv}{dt} = \frac{d}{dt} \ln i = \frac{d}{dt} \ln E - \frac{d}{dt} \ln A - \frac{d}{dt} K \ln I \quad (33)$$

or $$\Delta v = \Delta \ln i = -k \Delta \ln I \quad (34)$$

and inasmuch as it has previously been shown that $\Delta \ln I = \Delta E(\lambda) C_b d_b$, the voltage at the output of each channel corresponds to the absorption at the particular wavelength of light to which it is responsive. Similarly, a phototransistor or any other non-linear photoelectric device with a response of the form $i = AI_k$ could be used.

It will be apparent to those skilled in the art that the sample and hold circuits of FIGS. 1 and 4 are only one means for switching the electrical signals produced by the photosensitive devices into separate channels, and that the photosensitive devices themselves could perform this function. In such event, a logging means would be necessary in each channel. In fact, if desired, a separate logging means could be inserted in each channel in the arrangement shown in FIGS. 1 and 4.

In FIG. 1 the logging amplifier 34, the sample and hold circuit 38, and the bandpass amplifier 46 are means coupled to receive the electrical signals provided by the photosensitive device 32 and for deriving therefrom an output signal that is proportioned to the changes in the logarithm of the detected light corresponding to one wavelength of light. Similarly, the logging amplifier 34, the sample and hold circuit 40, and the bandpass amplifier 50 are means coupled to receive the electrical signals provided by the photosensitive device 32 and for deriving therefrom an output signal that is proportional to the A.C. component of the logarithm of the other transmitted wavelengths of light. When all of these components are combined, or when separate logging means is included in each channel, as described above, they form means coupled to receive the electrical signals from the photosensitive means 32 and to derive separate output signals that are respectively proportional to the alternating current component of the logarithm of the electrical signals. The same understanding applies to the arrangement of FIG. 4.

The measurement of cardiac output by indicator dilution techniques is based on FICK's principle, namely, by injecting a known amount of indicator into a stream of blood and measuring the concentration differences upstream and downstream from the injection site, a measurement of a flow rate may be calculated. The extension of this simple technique yields the familiar cardiac output calculation. The importance of the measurement is not questioned. However, the ideals of simplicity, speed, low cost, accuracy and non-invasiveness have yet to be met.

As previously described in a multiple wavelength section, the presence of a third absorber within the pulsatile blood stream may be dealt with by the addition of a third wavelength. If this wavelength is properly chosen for a particular dye, (cardio-green, methylene-blue, for example) the indicator concentration may be determined by using the same incremental absorbence techniques just described. Once this value is calculated the familiar cardiac output calculation may be completed.

Some of the advantages of using incremental absorbence techniques versus prior art for the dye concentration calculation are: that it eliminates the need for a cuvette, the withdrawal of blood samples, the plumbing for a flow-through cuvette and it is less invasive to the patient. Interfering fixed absorbers such as bone, hair, skin tissue, pigmentation, etc. are ignored as well as changes in the saturation of $HbO_2$. Moment to moment variations in the blood flow and blood velocity are automatically accounted for.

What is claimed is:

1. In apparatus for indicating the relative percentage of at least one absorber in (a) the arterial blood stream of living tissue, the combination of
    means for sequentially directing light of different wavelengths along a given path into which a member of a body may be inserted,
    photosensitive means for producing at its output electrical signals having amplitudes that respectively correspond to the intensity of the light of different ones of said wavelengths in said path,
    logarithmic means coupled to the output of said photosensitive means for deriving electrical signals that are proportioned to the logarithm of the electrical signals at the output of said photosensitive means, and
    separate means alternating current coupled to the output of said logarithmic means so as to receive only the alternating current components of the output of said logarithmic means, each said means deriving an output signal that respectively corresponds to the amplitude of the alternating current component of the electrical signal at the output of said logarithmic means corresponding to a different wavelength of light.

2. The combination as set forth in claim 1 wherein the frequency at which each wavelength of light is directed along said path is so high that the amount of pulsatile blood in a body member in said path cannot change significantly during a complete sequence of the lights.

3. A combination as set forth in claim 1 wherein means are provided for responding to said output signals so as to provide an indication of the percent of at least one absorber in the blood of a member of a body inserted in said path.

4. In an oximeter the combination of means for sequentially directing pulses of light of different wavelengths along a given path,
   photosensitive means for producing a first set of electrical pulse signals that respectively correspond to the intensity of said pulses of light as they may be modified by a member of a body placed in said path,
   a logging amplifier coupled to receive said first set of electrical pulse signals and produce at its output a second set of electrical pulses that respectively correspond to the logarithm of said first set,
   switching means coupled to the output of said logging amplifier for directing at least a portion of each of the pulses of said second set resulting from each wavelength of light to a different channel, and
   each of said channels including means for producing an output signal that is proportional to the peak to peak amplitude of the pulses directed to it by said switching means.

5. An instrument for non-invasively producing electrical signals that can be combined so as to determine the relative percentage of at least one absorber contained in the arterial blood of living tissue, comprising
   means for emitting radiations of different wavelengths along a path into which a member of a patient's body may be inserted,
   photosensitive means for providing first electrical signals, each of which corresponds to the received radiation strength of a different wavelength of light,
   logging means coupled to the output of said photosensitive means for providing second electrical signals, each respectively corresponding to the logarithm of one of said first electrical signals,
   means alternating current coupled to the output of said logging means so as to pass only the alternating current components of each of said second electrical signals to respectively different outputs, the alternating current components forming third electrical signals, and
   means for respectively deriving from each of said third electrical signals a separate electrical output signal proportional to the peak-to-peak amplitude of said third electrical signal.

6. An instrument as set forth in claim 5 wherein said last-mentioned means derived from each of said third electrical signals an electrical output signal proportional to average area of said third electrical signals above their minimum values.

7. Apparatus for non-invasively producing electrical signals that can be combined so as to determine the relative percentage of at least one absorber contained in the arterial blood stream of living tissue, comprising
   a light source,
   means for deriving a plurality of first signals, each representing the logarithm of the intensity of light of a different wavelength arriving at a given point in a path from said source, and
   means coupled to said latter means for deriving from each of said first signals a second signal corresponding to the peak-to-peak amplitude of the first signal during the period of at least one heart cycle.

* * * * *